United States Patent [19]
Hamery

[11] Patent Number: 6,070,693
[45] Date of Patent: Jun. 6, 2000

[54] HEARING PROTECTOR AGAINST LOUD NOISE

[75] Inventor: Pascal Hamery, Mulhouse, France

[73] Assignee: Institut Franco-Allemand de Recherches de Saint-Louis, Saint-Louis, France

[21] Appl. No.: 09/233,192

[22] Filed: Jan. 20, 1999

Related U.S. Application Data

[62] Division of application No. 08/994,015, Dec. 18, 1997, Pat. No. 5,936,208.

[30] Foreign Application Priority Data

Sep. 18, 1997 [FR] France .................................. 97.11623

[51] Int. Cl.[7] ........................................................ A61B 7/02
[52] U.S. Cl. .............................................................. 181/135
[58] Field of Search ..................... 181/130, 135; 128/864, 867; 2/209

[56] References Cited

U.S. PATENT DOCUMENTS

| | | |
|---|---|---|
| 4,587,965 | 5/1986 | De Boer et al. . |
| 4,852,683 | 8/1989 | Killion . |
| 5,113,967 | 5/1992 | Killion et al. . |
| 5,824,968 | 10/1998 | Packard et al. .......................... 181/131 |

*Primary Examiner*—Khanh Dang
*Attorney, Agent, or Firm*—Oliff & Berridge, PLC

[57] ABSTRACT

The invention relates to a hearing protector for attenuating, selectively or not, noises that can have an intensity of up to 190 dB, designed to be inserted in sealing fashion into the auditory canal. The hearing protector includes a flexible cylindrical body that has a ferrule at each end. At least one of the two ferrules has a channel that runs from one end of the ferrule to the center of the cylindrical body and contains an acoustic filter. When the two ferrules each contain an acoustic filter, the filters may or may not be identical.

17 Claims, 3 Drawing Sheets

HEARING PROTECTOR AGAINST LOUD NOISE

This is a Division of Application Ser. No. 08/994,015 filed Dec. 18, 1997, now U.S. Pat. No. 5,936,208. The entire disclosure of the prior application is hereby incorporated by reference herein in its entirety.

BACKGROUND OF THE INVENTION

1. Field of Invention

The invention relates to hearing protectors, and in particular, the invention relates to a hearing protector to protect against high, continuous or impulsed, noises. The hearing protector can function either in a selective attenuation mode or a maximum attenuation mode.

2. Description of Related Art

In the selective attenuation mode, sound attenuation is low for a specific range of frequencies and increases for sounds with frequencies above those in the specified range. Selective attenuation is especially effective for the loudest noises. A sample application of a hearing protector operating in the selective attenuation mode is the intelligible speech transmission in a noisy environment caused by impulsed noises, such as gunshots, for example. In this case, the frequency range in which the attenuation is low is between 100 Hz to 1000 Hz. In the maximum attenuation mode, the hearing protector stops all sounds throughout the frequency range, regardless of their intensity.

French Patent Publication No. 2 676 642, filed in the name of the Applicant, discloses a hearing protector that is not cumbersome and contacts the auditory canal. The protector comprises an elongate flexible body containing selective attenuation means, maximum attenuation means, and a manually controlled plug that makes it possible to choose the attenuation functional mode to be either selective or maximum. However, this device requires careful handling by the user who wants to block the auditory canal himself This manipulation can be done incorrectly, resulting in inefficient blockage in the selective or maximum attenuation modes.

SUMMARY OF THE INVENTION

The goal of the present invention is to provide a reliable hearing protector that does not suffer from the disadvantage of user adjustment and permits two configurations for noise attenuation that have different characteristics.

Another goal of the present invention is to provide a reliable hearing protector capable of selectively or automatically attenuating noises having intensities up to 190 dB. The hearing protector is intended to be sealingly inserted into the auditory canal of the user. The hearing protector includes a flexible cylindrical body having a ferrule at each end, with at least one of the ferrules having a channel that runs from one end of the ferrule to the center of the body and contains an acoustic filter.

The hearing protector has two ends, both of which can be inserted into the auditory canal and is referred to as a "double-ended" device. This contrasts with the well-known hearing protector that typically has one end that can be inserted into the auditory canal, while the other end allows the hearing protector to be gripped so the user can position it in the auditory canal. The present invention has two ends, that may or may not be identical, either of which can be inserted into the auditory canal, thus making it possible to choose between two operating modes of attenuation that may or may not be identical.

The device is useful in the fact that it possesses, in the same hearing protector, two configurations that can have different attenuation characteristics, both obtained by simply reversing the direction of the hearing protector, or ear plug, that is inserted into the auditory canal.

In a preferred embodiment, the two ferrules are separate parts linked by an internal connector. The internal connector may be a single cylinder pierced by a channel containing an acoustic filter, the cylinder forming a right angle that terminates at a first end of the channel and a second end at the center of the connector.

The internal connector may also be a single cylinder having a channel that terminates at three locations, such as at the center of the connector or at each end of the connector, with the parts of the channel terminating at the ends containing an acoustic filter that may or may not be identical.

The internal connector may also be composed of three cylindrical parts. The central part may have a channel at its center with a diameter slightly greater than that of the other two parts. The other two parts have a diameter that is essentially equal to or slightly larger than that of the channel. At least one of the two parts is pierced by a channel at its center which contains an acoustic filter and communicates with the channel in the central part. When the two parts each contain an acoustic filter, the filters may or may not be identical.

In an alternate embodiment, the internal connector may have serrations, or ridges, to hold the ferrules in place while in the auditory canal.

In yet another embodiment, the hearing protector may have tapered ends.

Preferably, each ferrule of the hearing protector is provided with an essentially hemispherical face of which the narrower side is intended to be inserted first into the auditory canal.

Advantageously, the body of the hearing protector may be provided with flexible annular fins having a diameter that increases from the inside to the outside of the auditory canal in order to wedgingly secure it in the auditory canal.

The hearing protector makes it possible to perform non-linear sound filtration by choosing the correct acoustic filter.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

Figure 1:
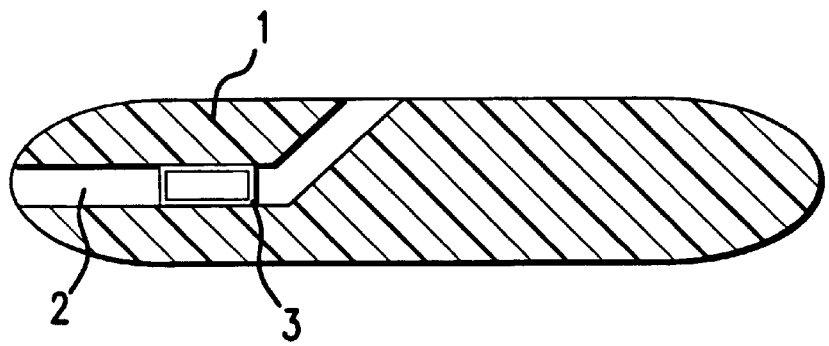
FIG. 1 is a longitudinal view, in partial section, of a "double-ended" hearing protector according to a preferred embodiment of the present invention.

FIG. 1 is a longitudinal view, in partial section, of the hearing protector according to one preferred embodiment of the present invention. The hearing protector includes a body 1 that is molded to fit in the auditory canal of the user. The body 1 is pierced by a channel 2 that runs from an end of the body 1 and terminates in the center of the body 1. The channel 2 contains an acoustic filter 3 that allows for example the selective and nonlinear filtration of sound. The other end of the body 1 is not perforated and allows maximum attenuation, regardless of the frequency and amplitude of the sound. Ideally, the body 1 has a length between 2 cm and 4 cm and is composed of a flexible material.

Figure 2:
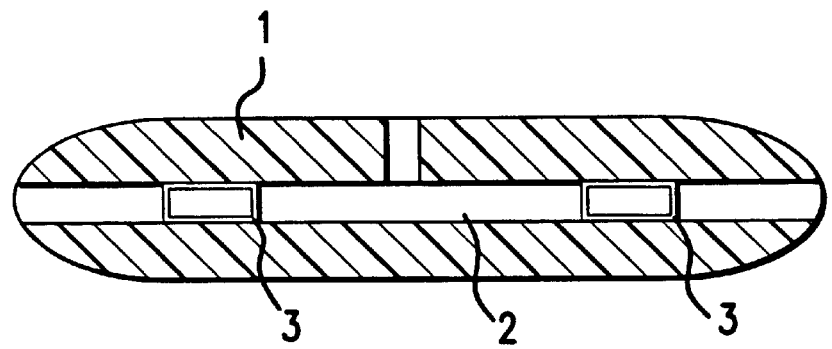
FIG. 2 is a longitudinal section view of a "double-ended" hearing protector according to a second embodiment of the present invention.

FIG. 2 is a longitudinal section view of the hearing protector according to a second embodiment of the present invention. The hearing protector includes a body 1 pierced by a channel 2 that terminates at each end of the body 1, as well as the center of body 1. The channel 2 also contains an acoustic filter 3 at each end. The filters may or may not be identical.

Figure 3:
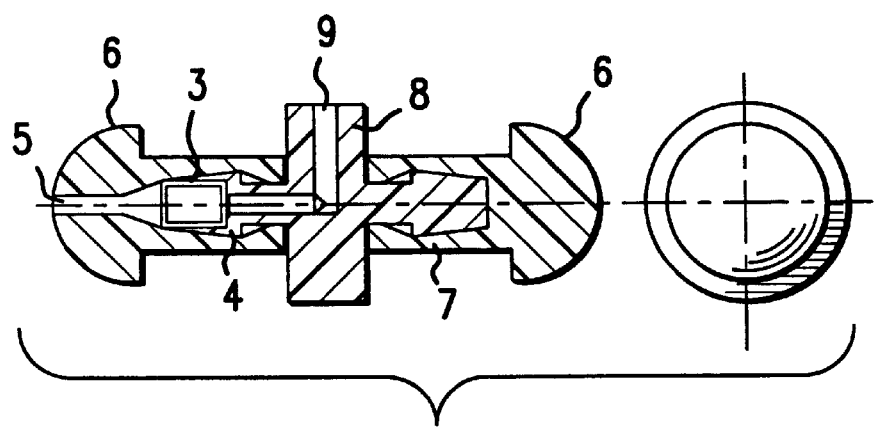
FIG. 3 is a longitudinal section view of a "double-ended" hearing protector according to a third embodiment of the present invention.

Referring to a third embodiment illustrated in FIG. 3, the hearing protector includes two cylindrical hollow ferrules 4 and 7 and an internal connector 8. The ferrules 4 and 7 are separate pieces that fit into one another and are joined by the internal connector 8 to keep the ferrules 4 and 7 together. Each ferrule 4 and 7 is provided with a substantially hemispherical face 6. The narrower portion of the face 6 is designed to be inserted first into the auditory canal. The substantially hemispherical face 6 ensures tightness between the hearing protector and the auditory canal. As illustrated in FIG. 3, at least one of the two ferrules, in this case, ferrule 4, is pierced by a channel 5 at its center. One of the two ends of the internal connector 8 that contains an acoustic filter 3 is inserted into at least one of the two ferrules 4 and 7. The acoustic filter 3 permits the selective non-linear filtration of sounds. The second ferrule, in this case, ferrule 7, need not be perforated and will allow maximum attenuation regardless of the frequency and amplitude of the sound. The internal connector 8 is pierced by a second channel 9 that connects at a first end with the first channel 5, which contains an acoustic filter 3, allowing for the use of the acoustic filter 3, and at a second end with the center of the connector 8. The second channel 9 is formed at a right angle to the channel 5.

Alternatively, in another embodiment, the internal connector 8 may also have a channel that extends in three locations, the center of the internal connector 8, as well as at each end of the internal connector 8. The portion of the channel that terminates at each end contains an acoustic filter 3 that may or may not be identical.

Figure 4A:
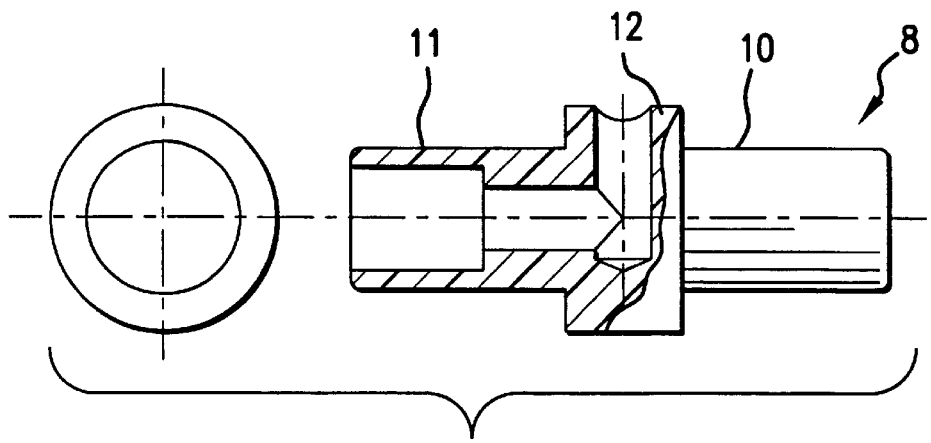
FIGS. 4a–4c are longitudinal views, in partial section, of different configurations of the internal connector that join the two ends of the hearing protector according to the present invention.

As shown in FIG. 4a, the internal connector 8 may include a single cylinder consisting of three cylindrical parts 10, 11, and 12. The central part 12 is pierced by a channel 9 at its center and has a diameter that is slightly larger than that of the other two parts 10 and 11. The two parts 10 and 11 have a diameter that is essentially equal to, but slightly larger than that of channel 5 in order to hold the assembly together. At least one of the two parts 10 and 11 is formed with channel 5, which contains an acoustic filter 3 and communicates with channel 9 in the central part 12, as shown in FIG. 5.

Figure 4B:
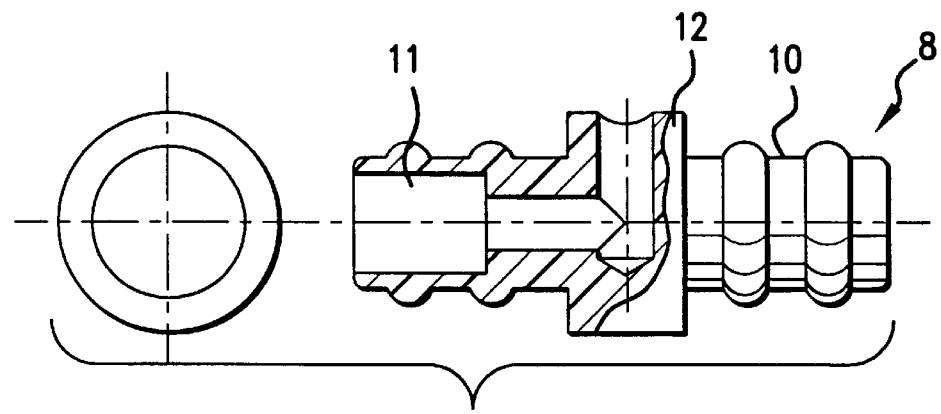
Figure 4C:
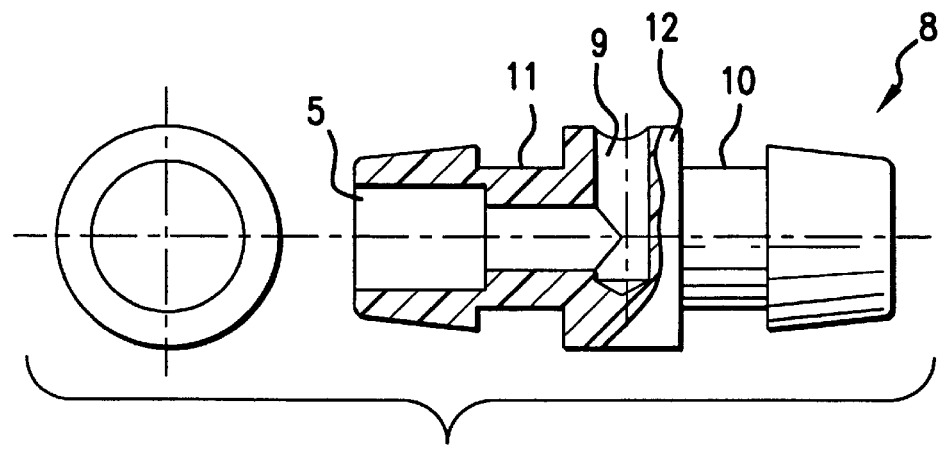
Figure 5:
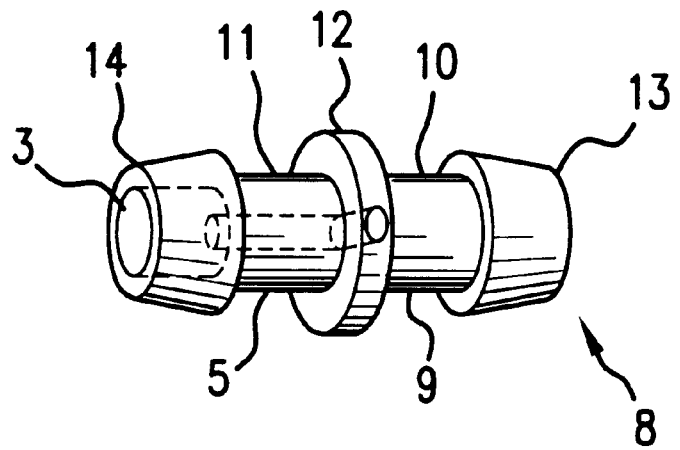
FIG. 5 is a perspective view of an internal connector for the two ends of the hearing protector according to an embodiment of the present invention.
Figure 6:
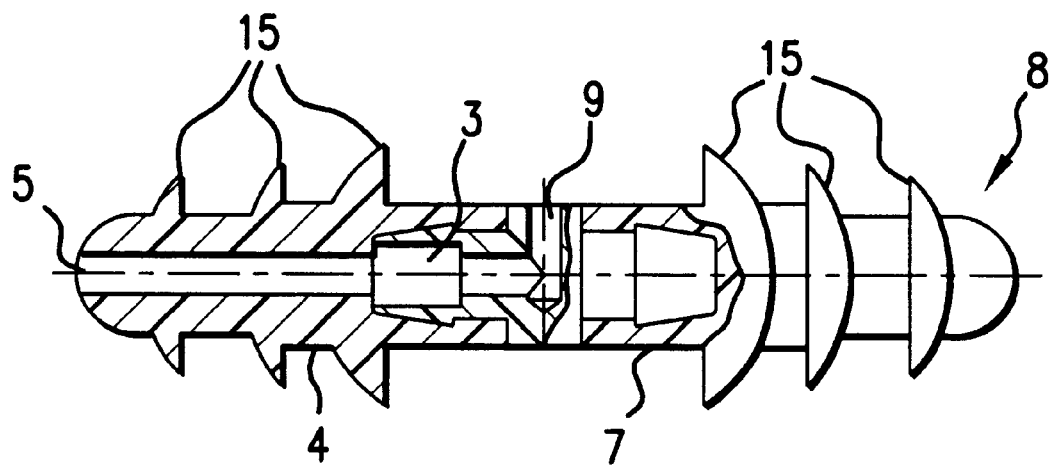
FIG. 6 is a longitudinal view, in partial section, of a hearing protector according to a fourth embodiment of the present invention.

The internal connector 8 may have serrations, or ridges, as shown in FIGS. 4b and 6, or the internal connector 8 may have tapered ends 13 and 14, as shown in FIGS. 4c and 5. In the case when the internal connector 8 is in three parts, the two parts 10 and 11 will have the serrations, ridges, or tapered ends 13 and 14.

One of the two ferrules has a perforation that, when joined to connector 8, is aligned with that of the central end of channel 9 located in part 12.

FIG. 6 is a longitudinal view, in partial section, of the hearing protector according to a fourth embodiment of the present invention. The hearing protector is provided with flexible annular fins 15 on the ferrules 4 and 7 to wedge the hearing protector against the walls of the auditory canal. The fins 15 may have a diameter that increases from the inside to the outside of the auditory canal.

The hearing protector, according to the present invention, is especially useful for individuals who are exposed to very loud engine and weapon noises, such as the crews of airplanes or military vehicles on exercises, for example. The hearing protector, according to the present invention, can also be used effectively by other personnel exposed to high-intensity noises in their working environments, such as construction sites and quarries for example.

While this invention has been described in conjunction with specific embodiments thereof, it is evident that many alternatives, modifications and variations will be apparent to those skilled in the art. Accordingly, the preferred embodiments of the invention as set forth herein are intended to be illustrative, not limiting. Various changes may be made without departing from the spirit and scope of the invention as defined in the following claims.

What is claimed is:

1. A hearing protector for selectively or automatically reducing noises having intensities up to 190 dB, the hearing protector being intended to be sealingly inserted into an auditory canal of a user, the hearing protector comprising:
   a cylindrical body having a center, a first end and a second end;
   a channel extending from said first and second ends to said center of said cylindrical body; and
   said channel containing a first acoustic filter and a second acoustic filter, each of said first and second filters being in communication with one of said first and second ends.

2. The hearing protector according to claim 1, wherein said first and second acoustic filters are identical.

3. The hearing protector according to claim 1, wherein said first and second acoustic filters are not identical.

4. The hearing protector according to claim 1, further having a ferrule at each of said first and second ends wherein said ferrules are separate and said cylindrical body forms an internal connector linking said ferrules.

5. The hearing protector according to claim 4, wherein said internal connector is a single cylinder, said channel forming a right angle and having a first end of said channel containing said first acoustic filter and terminating at at least one of said ferrules and a second end of said channel terminating in said center of said internal connector.

6. The hearing protector according to claim 4, wherein said channel in said internal connector terminates at said center of said internal connector and at said first end and said second end of said internal connector, said first end containing said first acoustic filter and said second end containing said second acoustic filter.

7. The hearing protector according to claim 6, wherein said first acoustic filter is identical to said second acoustic filter.

8. The hearing protector according to claim 6, wherein said first acoustic filter is not identical to said second acoustic filter.

9. The hearing protector according to claim 4, wherein said internal connector includes a central cylindrical part having a central diameter, a first cylindrical part having a first diameter and a second cylindrical part having a second diameter, said central diameter being larger than said first diameter and said second diameter, said first diameter and said second diameter being larger than said channel, said first cylindrical part containing said first acoustic filter and said second cylindrical part contains said second acoustic filter.

10. The hearing protector according to claim 9, wherein said first acoustic filter and said second acoustic filter are identical.

11. The hearing protector according to claim 9, wherein said first acoustic filter and said second acoustic filter are not identical.

12. The hearing protector according to claim 4, wherein said internal connector has serrations for securing said ferrules to said internal connector.

13. The hearing protector according to claim 4, wherein said internal connector has ridges for securing said ferrules to said internal connector.

14. The hearing protector according to claim 4, wherein said internal connector has tapered ends.

15. The hearing protector according to claim 1, wherein said ferrules each have an essentially hemispherical face having a narrow side, said narrow sides being designed to be inserted into the auditory canal of the user first.

16. The hearing protector of claim 1, wherein said cylindrical body is provided with annular fins, said fins having a diameter that increases from said first and second ends of said cylindrical body toward said center of said cylindrical body, the hearing protector being wedgingly securable within the auditory canal of the user.

17. The hearing protector according to claim 1, wherein said acoustic filters permit non-linear filtration of sound.

* * * * *